United States Patent
Sohn et al.

(10) Patent No.: US 12,090,220 B2
(45) Date of Patent: Sep. 17, 2024

(54) EFFICIENT SUNSCREEN COMPOSITIONS WITH DIETHYLAMINO HYDROXYBENZOYL HEXYL BENZOATE, BUTYL METHOXYDIBENZOYLMETHANE AND ORGANIC PARTICULATE UV FILTER

(71) Applicant: BASF SE, Ludwigshafen am Rhein (DE)

(72) Inventors: Myriam Sohn, Grenzach-Wyhlen (DE); Stanislaw Krus, Grenzach-Wyhlen (DE); Marcel Schnyder, Grenzach-Wyhlen (DE); Stephanie Acker, Grenzach-Wyhlen (DE)

(73) Assignee: BASF SE, Ludwigshafen am Rhein (DE)

( * ) Notice: Subject to any disclaimer, the term of this patent is extended or adjusted under 35 U.S.C. 154(b) by 114 days.

(21) Appl. No.: 17/439,608

(22) PCT Filed: Mar. 13, 2020

(86) PCT No.: PCT/EP2020/056916
§ 371 (c)(1),
(2) Date: Sep. 15, 2021

(87) PCT Pub. No.: WO2020/187766
PCT Pub. Date: Sep. 24, 2020

(65) Prior Publication Data
US 2022/0175641 A1 Jun. 9, 2022

(30) Foreign Application Priority Data
Mar. 15, 2019 (EP) .................... 19163168

(51) Int. Cl.
*A61K 8/35* (2006.01)
*A61K 8/41* (2006.01)
*A61K 8/49* (2006.01)
*A61Q 17/04* (2006.01)

(52) U.S. Cl.
CPC ............ *A61K 8/35* (2013.01); *A61K 8/411* (2013.01); *A61K 8/4966* (2013.01); *A61Q 17/04* (2013.01); *A61K 2800/30* (2013.01)

(58) Field of Classification Search
CPC ...................................................... A61K 8/35
See application file for complete search history.

(56) References Cited

U.S. PATENT DOCUMENTS

| | | |
|---|---|---|
| 2003/0152532 A1 | 8/2003 | Candau |
| 2003/0161793 A1 | 8/2003 | Candau |
| 2005/0008587 A1 | 1/2005 | Schulz et al. |
| 2012/0128611 A1 | 5/2012 | Grumelard et al. |
| 2013/0251650 A1 | 9/2013 | Winkler et al. |
| 2018/0200170 A1 | 7/2018 | Herzog et al. |

FOREIGN PATENT DOCUMENTS

| | | | |
|---|---|---|---|
| CN | 101808615 A | 8/2010 | |
| CN | 102470081 A | 5/2012 | |
| CN | 106659653 A | 5/2017 | |
| EP | 2092930 A1 * | 8/2009 | ............ A61K 8/062 |
| EP | 2837407 A2 | 2/2015 | |
| EP | 3093006 A1 | 11/2016 | |
| EP | 3093007 A1 | 11/2016 | |
| EP | 3093008 A1 | 11/2016 | |
| EP | 3195853 A1 | 7/2017 | |
| EP | 3351236 A1 | 7/2018 | |
| JP | 2005-511585 A | 8/2005 | |
| JP | 2012-532837 A | 12/2012 | |
| JP | 2017-521463 A | 8/2017 | |
| WO | 2013/076075 A2 | 5/2013 | |
| WO | 2013/076075 A3 | 9/2013 | |
| WO | 2016/012586 A1 | 1/2016 | |

OTHER PUBLICATIONS

International Search Report and Written Opinion received for PCT Patent Application No. PCT/EP2020/056916, mailed on Jun. 8, 2020, 12 pages.
International Preliminary Report on Patentability received for PCT Patent Application No. PCT/EP2020/056916, mailed on Sep. 30, 2021, 11 pages.
Mintel GNDP "50+SPF Spray Lotion", RoC, ID:6344725, URL: https://www.gnpd.com, May 2006.

* cited by examiner

*Primary Examiner* — Benjamin J Packard
(74) *Attorney, Agent, or Firm* — Faegre Drinker Biddle & Reath LLP

(57) ABSTRACT

The present invention relates to sunscreen or daily care compositions comprising hexyl 2-[4-(diethylamino)-2-hydroxybenzoyl]benzoate (INCI diethylamino hydroxybenzoyl hexyl benzoate), 1-(4-(1,1-dimethylethyl)phenyl)-3-(4-methoxyphenyl)propane-1,3-dione (INCI butyl methoxydibenzoylmethane) and at least one organic particulate UV filter, wherein the composition does not comprise 2-hydroxy-4-methoxybenzophenone (INCI oxybenzone) and ethylhexyl-2-cyano-3,3-diphenyl-acrylate (INCI octocrylene).

13 Claims, No Drawings

EFFICIENT SUNSCREEN COMPOSITIONS WITH DIETHYLAMINO HYDROXYBENZOYL HEXYL BENZOATE, BUTYL METHOXYDIBENZOYLMETHANE AND ORGANIC PARTICULATE UV FILTER

CROSS-REFERENCE TO RELATED APPLICATIONS

This application is a national stage application (under 35 U.S.C. § 371) of PCT/EP2020/056916, filed Mar. 13, 2020, which claims benefit of European Application No. 19163168.8, filed Mar. 15, 2019, both of which are incorporated herein by reference in their entirety.

The present invention relates to sunscreen or daily care compositions comprising hexyl 2-[4-(diethylamino)-2-hydroxybenzoyl]benzoate (INCI diethylamino hydroxybenzoyl hexyl benzoate), 1-(4-(1,1-dimethylethyl)phenyl)-3-(4-methoxyphenyl)propane-1,3-dione (INCI butyl methoxydibenzoylmethane) and at least one organic particulate UV filter, wherein the composition does not comprise 2-hydroxy-4-methoxybenzophenone (INCI oxybenzone) and ethylhexyl-2-cyano-3,3-diphenyl-acrylate (INCI octocrylene).

UV radiation causes harmful effects on the human skin. Beside the acute effect of sunburn of the skin, UV radiation is also known to increase the risk of skin cancer. Furthermore, long time exposure to UV-A and UV-B light can cause phototoxic and photo allergenic reactions on the skin and can accelerate skin aging.

To protect the human skin from UV radiation, various sun protecting UV filters (also referred to as UV absorbers) exist including UV-A filter, UV-B filter and broadband filters. These filters are added to sunscreen or cosmetic compositions. The UV filters are either organic or inorganic, particulate or non-particulate compounds, of which all have a high absorption efficacy in the UV-light range. In general, UV light can be divided into UV-A radiation and UV-B radiation. Depending on the position of the absorption maxima, UV-filters are divided into UV-A and UV-B filters. In case an UV-filter absorbs both, UV-A and UV-B light, it is referred to as a broadband absorber.

Since 2006, the EU commission has recommended that all sunscreen or cosmetic compositions should have an UV-A protection factor, which is at least one third of the labelled sun protection factor (SPF), wherein the sun protection factor refers mainly to the UV-B protection.

However, the UV filters known in the prior art which are used in sunscreen or cosmetic compositions have certain disadvantages. In particular, it is referred to the disadvantage of certain UV filter, which are frequently under discussion due to their health and environmental concern, although they are approved for being used in sunscreen or cosmetic compositions. UV filter under discussion are for example octocrylene, oxybenzone, homosalate or ethylhexyl methoxy cinnamate.

Another disadvantage results from the use of dibenzoylmethane derivatives, e.g. butyl methoxydibenzoylmethane, which are known to be relatively sensitive to UV radiation. This negative effect does not make it possible to provide a constant protection during prolonged exposure to the sun. Therefore, repeated applications of sunscreen compositions comprising the same are necessary to provide an efficient protection for the user.

Therefore, there is a need for sunscreen or cosmetic compositions of the daily use, which are efficient for sun protection but free of UV filter under discussion. Furthermore, there is a need for sunscreen or daily care compositions, which are photo stable under UV radiation.

EP 2 837 407 A2 discloses odor stable, octocrylene free cosmetic compositions comprising one or more UV filter selected from triazine derivatives, titanium dioxide, butyl methoxydibenzoylmethane and/or diethylamino hydroxybenzoyl hexyl benzoate, wherein the composition is free of ethylhexyl salicylate, octocrylene, homomenthylsalicylate and ethylhexyl methoxy cinnamate.

EP 3 093 008 A1 refers to a sunscreen composition which is free of octocrylene and comprises diethylamino hydroxybenzoyl hexyl benzoate, phenylbenzimidazole sulfonic acid, and one or more salicylates selected from ethylhexyl salicylate and homosalate.

EP 3 093 007 A1 discloses a cosmetic composition comprising a UV filter combination of diethylamino hydroxybenzoyl hexyl benzoate, ethylhexyl triazone and one or more salicylates selected from ethylhexyl salicylate and homosalate, wherein the composition may further be free of oxybenzone, octocrylene and 4-methylbenzylidene camphor.

EP 3 093 006 relates to an alcohol containing, octocrylene free sunscreen composition. The cosmetic composition comprises a UV filter combination of diethylamino hydroxybenzoyl hexyl benzoate, ethylhexyl triazone, and bis-ethylhexylphenol methoxyphenyl triazine, wherein the composition comprises one or more alcohols.

EP 3 195 853 A1 discloses an octocrylene free sunscreen composition, wherein the cosmetic composition comprises a UV filter combination of diethylamino hydroxybenzoyl hexyl benzoate, diethyl butamido triazone and ethylhexyl triazone.

EP 3 351 236 A1 relates to a cosmetic composition comprising a UV filter combination of diethylamino hydroxybenzoyl hexyl benzoate, butyl methoxydibenzoylmethane and polyglycerol fatty acid esters, wherein the composition is free of 4-methylbenzylidene camphor, oxybenzone, ethylhexyl methoxycinnamate, isoamyl p-methoxycinnamate and octocrylene.

US 2003/0161793 A1 discloses a topically applicable cosmetic/dermatological sunscreen composition devoid of any p-methylbenzylidene camphor but contains at least one UV-screening dibenzoylmethane compound and at least one UV-screening amino-substituted 2-hydroxybenzophenone compound of the structural formula (1).

US 2003/0152532 A1 relates to topically applicable cosmetic/dermatological sunscreen compositions comprising particulates of at least one insoluble organic UV-screening agent and at least one UV screening amino-substituted 2-hydroxybenzophenone compound.

US 2012/0128611 discloses a UV filter combination comprising a first UV filter selected from benzylidene malonates and a second UV filter selected from a specific group for the protection of human and animal hair and skin against UV radiation.

Therefore, it has been an object of the present invention to provide efficient sunscreen or daily care compositions. It has been another object of the present invention to provide efficient sunscreen or daily care compositions, which perfectly meet the consumers demands with respect to performance criteria such as good solubility and stability of the UV filters in the product, particularly in the absence of the critical UV filters as mentioned above. In this connection, it has been another object of the present invention to provide sunscreen or daily care compositions, which are free of UV filters under discussion.

It has surprisingly been found that at least one of these objects can be achieved by the sunscreen or daily care composition according to the present invention.

In particular, the inventors of the present application found that the sunscreen or daily care composition according to the present invention provides an efficient UV-A and UV-B protection, nevertheless the composition is free of UV filter under discussion. Furthermore, it has surprisingly been found by the inventors of the present application that the sunscreen or daily care composition according to the present invention is photo stable.

Thus, according to one embodiment, the present invention relates to a sunscreen or daily care composition comprising
(i) hexyl 2-[4-(diethylamino)-2-hydroxybenzoyl]benzoate (INCI diethylamino hydroxybenzoyl hexyl benzoate); and
(ii) 1-(4-(1,1-dimethylethyl)phenyl)-3-(4-methoxyphenyl)propane-1,3-dione (INCI butyl methoxydibenzoylmethane); and
(iii) at least one organic particulate UV filter;
wherein the composition does not comprise 2-hydroxy-4-methoxybenzophenone (INCI oxybenzone) and ethylhexyl-2-cyano-3,3-diphenyl-acrylate (INCI octocrylene).

In a preferred embodiment of said composition, the sunscreen or daily care composition does not comprise 2-ethylhexyl-(2E)-3-(4-methoxyphenyl)acrylate (INCI ethylhexyl methoxy cinnamate) and isoamyl-4-methoxycinnamate (INCI isoamyl-p-methoxy cinnamate).

In another preferred embodiment of said composition, the sunscreen or daily care composition is free of parabens.

In another preferred embodiment of said composition, in the sunscreen or daily care composition the at least one organic particulate UV filter is selected from the group consisting of 2,2'-methylene bis[6-(2H-benzotriazol-2-yl)-4-(1,1,3,3-tetramethylbutyl)phenol] (INCI methylene bis-benzotriazolyl tetramethylbutylphenol), 2,4,6-tris(biphenyl-4-yl)-1,3,5-triazine (INCI trisbiphenyl triazine), 1,1'-(1,4-piperazinediyl)bis[1-[2-[4-(diethylamino)-2-hydroxybenzoyl]phenyl]-methanone (INCI bis-(diethylaminohydroxybenzoyl benzoyl) piperazine), 5,6,5',6'-tetraphenyl-3-3'-(1,4-phenylene)bis(1,2,4-triazine) (INCI phenylene bis-diphenyltriazine), micronized 1,4-di(benzoxazole-2'-yl)benzene and combinations thereof.

In a more preferred embodiment of said composition, in the sunscreen or daily care composition the at least one organic particulate UV filter is selected from the group consisting of 2,2'-methylene bis[6-(2H-benzotriazol-2-yl)-4-(1,1,3,3-tetramethylbutyl)phenol] (INCI methylene bis-benzotriazolyl tetramethylbutylphenol), 2,4,6-tris(biphenyl-4-yl)-1,3,5-triazine (INCI trisbiphenyl triazine), 5,6,5',6'-tetraphenyl-3-3'-(1,4-phenylene)bis(1,2,4-triazine) (INCI phenylene bis-diphenyltriazine) and combinations thereof.

In another preferred embodiment of said composition, the sunscreen or daily care composition is free of phenoxyethanol.

In another preferred embodiment of said composition, the sunscreen or daily care composition comprises hexyl 2-[4-(diethylamino)-2-hydroxybenzoyl]benzoate (INCI diethylamino hydroxybenzoyl hexyl benzoate) in an amount of from 1% to 10% by weight, based on the total weight of the composition.

In another preferred embodiment of said composition, the sunscreen or daily care composition comprises 1-(4-(1,1-dimethylethyl)phenyl)-3-(4-methoxyphenyl)propane-1,3-dione (INCI butyl methoxydibenzoylmethane) in an amount of from 1% to 5% by weight, based on the total weight of the composition.

In another preferred embodiment of said composition, the sunscreen or daily care composition comprises the at least one organic particulate UV filter in an amount of from 0.5% to 10% by weight, based on the total weight of the composition.

In another preferred embodiment of said composition, the sunscreen or daily care composition further comprises at least one UV filter selected from 4,4',4''-(1,3,5-triazine-2,4,6-triyltriimino)tris-benzoic acid-tris(2-ethylhexyl)ester (INCI ethylhexyl triazone), 4,4'-[[6-[[4-[[(1,1-dimethylethyl)amino]carbonyl]phenyl]amino]-1,3,5-triazin-2,4-diyl]diimino]bis-benzoic acid-bis(2-ethylhexyl)ester (INCI diethylhexyl-butamidotriazone), 2,4-bis-{[4-(2-ethyl-hexyloxy)-2-hydroxy]-phenyl}-6-(4-methoxyphenyl)-1,3,5 triazine (INCI bis-ethylhexyloxyphenol methoxyphenyl triazine) and combinations thereof.

In another preferred embodiment of said composition, the sunscreen or daily care composition comprises perfume.

In a more preferred embodiment of said composition, the sunscreen or daily care composition comprises
(i) hexyl 2-[4-(diethylamino)-2-hydroxybenzoyl]benzoate (INCI diethylamino hydroxybenzoyl hexyl benzoate); and
(ii) 1-(4-(1,1-dimethylethyl)phenyl)-3-(4-methoxyphenyl)propane-1,3-dione (INCI butyl methoxydibenzoylmethane); and
(iii) 2,2'-methylene bis[6-(2H-benzotriazol-2-yl)-4-(1,1,3,3-tetramethylbutyl)phenol] (INCI methylene bis-benzotriazolyl tetramethylbutylphenol);
wherein the composition does not comprise 2-hydroxy-4-methoxybenzophenone (INCI oxybenzone) and ethylhexyl-2-cyano-3,3-diphenyl-acrylate (INCI octocrylene).

In another preferred embodiment of said composition, the sunscreen or daily care composition comprises (iii) to (ii) in a ratio of 1:1.

In another preferred embodiment of said composition, the sunscreen or daily care composition comprises hexyl 2-[4-(diethylamino)-2-hydroxybenzoyl]benzoate (INCI diethylamino hydroxybenzoyl hexyl benzoate) in an amount of from 1% to 8% by weight, based on the total weight of the composition.

In another preferred embodiment of said composition, the sunscreen or daily care composition comprises 1-(4-(1,1-dimethylethyl)phenyl)-3-(4-methoxyphenyl)propane-1,3-dione (INCI butyl methoxydibenzoylmethane) in an amount of from 1% to 5% by weight, based on the total weight of the composition.

In another preferred embodiment of said composition, the sunscreen or daily care composition comprises 2,2'-methylene bis[6-(2H-benzotriazol-2-yl)-4-(1,1,3,3-tetramethylbutyl)phenol] (INCI methylene bis-benzotriazolyl tetramethylbutylphenol) in an amount of from 1% to 10% by weight, based on the total weight of the composition.

In a second embodiment, the present invention relates to a sunscreen or daily care composition comprising
(i) hexyl 2-[4-(diethylamino)-2-hydroxybenzoyl]benzoate (INCI diethylamino hydroxybenzoyl hexyl benzoate) in an amount of from 1% to 9% by weight, based on the total weight of the composition; and
(ii) 1-(4-(1,1-dimethylethyl)phenyl)-3-(4-methoxyphenyl)propane-1,3-dione (INCI butyl methoxydibenzoylmethane); and
(iii) at least one organic particulate UV filter; and
(iv) at least one emollient with a polarity index of <30 mN/m
wherein the composition does not comprise 2-hydroxy-4-methoxybenzophenone (INCI oxybenzone), ethylhexyl-2- cyano-3,3-diphenyl-acrylate (INCI octocrylene) and benzylidene malonates according to the following preferred structures:

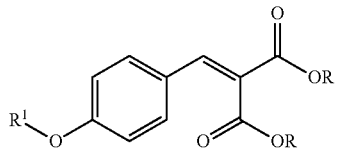

wherein
R¹ is methyl, ethyl, propyl or n-butyl;
if R¹ is methyl, then
R is tert. butyl or a radical of formula

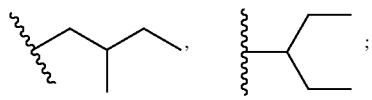

or a radical of formula

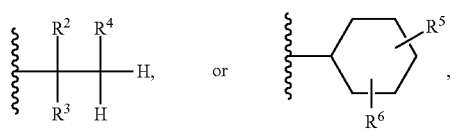

wherein
$R^2$ and $R^3$ are independently from each other hydrogen or methyl;
$R^4$ is methyl, ethyl or n-propyl;
$R^5$ and $R^6$ are independently from each other hydrogen or $C_1$-$C_3$-alkyl;
if $R^1$ is ethyl, propyl or n-butyl, then
R is isopropyl.

In a preferred embodiment of said second embodiment of said composition, the sunscreen or daily care composition does not comprise 2-ethylhexyl-(2E)-3-(4-methoxyphenyl) acrylate (INCI ethylhexyl methoxy cinnamate) and isoamyl-4-methoxycinnamate (INCI isoamyl-p-methoxy cinnamate).

In another preferred embodiment of said second embodiment of said composition, the sunscreen or daily care composition is free of parabens.

In another preferred embodiment of said second embodiment of said composition, in the sunscreen or daily care composition the at least one organic particulate UV filter is selected from the group consisting of 2,2'-methylene bis[6-(2H-benzotriazol-2-yl)-4-(1,1,3,3-tetramethylbutyl)phenol] (INCI methylene bis-benzotriazolyl tetramethylbutylphenol), 2,4,6-tris(biphenyl-4-yl)-1,3,5-triazine (INCI trisbiphenyl triazine), 1,1'-(1,4-piperazinediyl)bis[1-[2-[4-(diethylamino)-2-hydroxybenzoyl]phenyl]-methanone (INCI bis-(diethylaminohydroxybenzoyl benzoyl) piperazine), 5,6,5', 6'-tetraphenyl-3-3'-(1,4-phenylene)bis(1,2,4-triazine) (INCI phenylene bis-diphenyltriazine), micronized 1,4-di(benzoxazole-2'-yl)benzene and combinations thereof.

In a more preferred embodiment of said second embodiment of said composition, in the sunscreen or daily care composition the at least one organic particulate UV filter is selected from the group consisting of 2,2'-methylene bis[6-(2H-benzotriazol-2-yl)-4-(1,1,3,3-tetramethylbutyl)phenol] (INCI methylene bis-benzotriazolyl tetramethylbutylphenol), 2,4,6-tris(biphenyl-4-yl)-1,3,5-triazine (INCI trisbiphenyl triazine), 5,6,5',6'-tetraphenyl-3-3'-(1,4-phenylene) bis(1,2,4-triazine) (INCI phenylene bis-diphenyltriazine) and combinations thereof.

In another preferred embodiment of said second embodiment of said composition, the sunscreen or daily care composition is free of phenoxyethanol.

In another preferred embodiment of said second embodiment of said composition, the composition comprises hexyl 2-[4-(diethylamino)-2-hydroxybenzoyl]benzoate (INCI diethylamino hydroxybenzoyl hexyl benzoate) in an amount of from 2% to 8% by weight, preferably in an amount of from 4% to 6% by weight, based on the total weight of the composition.

In another preferred embodiment of said second embodiment of said composition, the sunscreen or daily care composition comprises 1-(4-(1,1-dimethylethyl)phenyl)-3-(4-methoxyphenyl)propane-1,3-dione (INCI butyl methoxydibenzoylmethane) in an amount of from 1% to 5% by weight, based on the total weight of the composition.

In another preferred embodiment of said second embodiment of said composition, the sunscreen or daily care composition comprises the at least one organic particulate UV filter in an amount of from 0.5% to 10% by weight, based on the total weight of the composition.

In another preferred embodiment of said second embodiment of said composition, the sunscreen or daily care composition further comprises at least one UV filter selected from 4,4',4''-(1,3,5-triazine-2,4,6-triyltriimino)tris-benzoic acid-tris(2-ethylhexyl)ester (INCI ethylhexyl triazone), 4,4'-[[6-[[4-[[(1,1-dimethylethyl)amino]carbonyl]phenyl] amino]-1,3,5-triazin-2,4-diyl]diimino]bis-benzoic acid-bis (2-ethylhexyl)ester (INCI diethylhexyl-butamidotriazone), 2,4-bis-{[4-(2-ethyl-hexyloxy)-2-hydroxy]-phenyl}-6-(4-methoxyphenyl)-1,3,5 triazine (INCI bis-ethylhexyloxyphenol methoxyphenyl triazine) and combinations thereof.

In another preferred embodiment of said second embodiment of said composition, the sunscreen or daily care composition comprises at least one perfume.

In another preferred embodiment of said second embodiment of said composition, the at least one particulate UV filter (iii) is 2,2'-methylene bis[6-(2H-benzotriazol-2-yl)-4-(1,1,3,3-tetramethylbutyl)phenol] (INCI methylene bis-benzotriazolyl tetramethylbutylphenol).

In another preferred embodiment of said second embodiment of said composition, the composition comprises (iii) to (ii) in a ratio of 1:1.

In another preferred embodiment of said second embodiment of said composition, the at least one emollient with a polarity index of <30 mN/m is selected from esters of linear or branched fatty acids with linear or branched fatty alcohols, di- and tricarboxylic acid esters with linear or branched alcohols, esters of hydroxycarboxylic acids with linear or branched fatty alcohols, esters of linear or branched fatty acids with polyhydric alcohol and mono-, di-, and triglycerides based on $D_6$-$D_{18}$ fatty acids.

In a further aspect, the present invention relates to the use of hexyl 2-[4-(diethylamino)-2-hydroxybenzoyl]benzoate (INCI diethylamino hydroxybenzoyl hexyl benzoate) and at least one organic particulate UV filter for photostabilizing 1-(4-(1,1-dimethylethyl)phenyl)-3-(4-methoxyphenyl)propane-1,3-dione (INCI butyl methoxydibenzoylmethane) in a sunscreen or daily care composition, wherein the composition does not comprise 2-hydroxy-4-methoxybenzophenone (INCI oxybenzone) and ethylhexyl-2-cyano-3,3-diphenyl-acrylate (INCI octocrylene).

Before describing preferred embodiments of the present invention in detail, definitions important for understanding the present invention are given.

As used in this specification and in the appended claims, the singular forms of "a" and "an" also include the respective plurals unless the context clearly dictates otherwise. In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%. It is to be understood that the term "comprising" is not limiting. For the purposes of the present invention, the term "consisting of" is considered to be a preferred embodiment of the term "comprising of". If hereinafter a group is defined to comprise at least a certain number of embodiments, this is meant to also encompass a group, which preferably consists of these embodiments only.

Furthermore, the terms "first", "second", "third" or "(i)", "(ii)", "(iii)", "(iv)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

As used herein the term "free of" in the context that the composition of the present invention is free of a specific compound or group of compounds, which may be combined under a collective term, means that the composition does not comprise said compound or group of compounds in an amount of more than 0.8% by weight, based on the total weight of the composition. Furthermore, it is preferred that the composition according to the present invention does not comprise said compounds or group of compounds in an amount of more than 0.5% by weight, preferably the composition does not comprise said compounds or group of compounds at all. The same definition is applied for the term "does not comprise". Furthermore, it is to be understood that the term "free of" or "does not comprise", in case the composition does not comprise a compound X and a compound Y means that the compositions must be free of both compounds X and Y. In other words, the composition may not contain any compound selected from X and Y.

The term "sunscreen composition" refers to any topical product, which reflects and/or absorbs certain parts of UV radiation. Thus, the term "sunscreen composition" is to be understood as not only including sunscreen compositions, but also any cosmetic compositions that provide UV protection. The term "topical product" refers to a product that is applied to the skin and can refer, e.g., to sprays, lotions, creams, oils, or gels. The sunscreen composition may comprise one or more active agents, e.g., organic or inorganic UV filters, as well as other ingredients or additives, e.g., emulsifiers, emollients, viscosity regulators, stabilizers, preservatives, or fragrances.

The term "daily care composition" refers to any topical product, which reflects or absorbs certain parts of UV radiation and is used as an everyday care product for the human body, e.g., for face, body or hair. The daily care composition may comprise one or more active agents, e.g., organic or inorganic UV filters, as well as other ingredients or additives, e.g., emulsifiers, emollients, viscosity regulators, stabilizers, preservatives, or fragrances.

The term "sun protection factor (SPF)" as used herein indicates how well the skin is protected by a sunscreen composition mainly from UV-B radiation. In particular, the factor indicates how much longer the protected skin may be exposed to the sun without getting a sunburn in comparison to untreated skin. For example, if a sunscreen composition with an SPF of 15 is evenly applied to the skin of a person usually getting a sunburn after 10 minutes in the sun, the sunscreen allows the skilled person to stay in the sun 15 times longer. In other words, SPF 15 means that $\frac{1}{15}$ of the burning UV radiation will reach the skin, assuming sunscreen is applied evenly at a thick dosage of 2 milligrams per square centimeter ($mg/cm^2$).

The term "UV-filter" as used herein refers to organic or inorganic compounds, which can absorb or reflect UV radiation caused by sunlight. UV-filter can be classified based on their UV protection curve as UV-A, UV-B or broadband filters. In the context of the present application, broadband filters may be listed as UV-A filters, as they also provide UV-A protection. In other words, preferred UV-A filters also include broadband filters.

Particulate UV filters can be further divided into organic particulate UV filters and inorganic particulate UV filters. While organic particulate UV filters are based on organic compounds, inorganic particulate UV filters are based on inorganic compounds such as titanium dioxide. In the sunscreen composition, particulate UV filters will be present in particulate form, as their solubility is less than 0.01% by weight, preferably less than 0.05% by weight in the sunscreen composition, i.e. in the water and the cosmetic oils contained therein. Preferably, the particulate UV filters have a particle size $D_N50$ determined by light scattering of less than 2000 nm, preferably less than 1000 nm, wherein $D_N50$ refers to the particle size value, where half of the population lies below this value, and half of the population lies above this value, i.e. the median value of the particle size volume distribution.

The term "photostabilizer" or "photostabilization" refers to compounds or UV filter, which prevent other UV filters from undergoing degradation processes upon UV radiation or by destabilization of the presence of other compounds, which can be for example another UV filter. Photostabilizer either protect the UV filter by structural or geometrical means, or by dissipating energy from the UV filter in order to reduce the possibility of destabilization.

Hexyl 2-[4-(diethylamino)-2-hydroxybenzoyl]benzoate (INCI diethylamino hydroxybenzoyl hexyl benzoate) is an oil soluble UV-A filter, which has an absorption maximum at 354 nm. Diethylamino hydroxybenzoyl hexyl benzoate has an excellent photo stability for long-lasting protection of the skin and provides an efficient shielding against UV-A I and UV-A II radiation. It is sold under the trade name Uvinul® A Plus by BASF.

1-(4-(1,1-dimethylethyl)phenyl)-3-(4-methoxyphenyl) propane-1,3-dione (INCI butyl methoxydibenzoylmethane) is a soluble organic UV-A filter. It absorbs UV-A radiation in the range of from 320 nm to 400 nm with an absorption maximum at 357 nm.

2-Hydroxy-4-methoxybenzophenone (INCI oxybenzone) absorbs UV-A light as well as UV-B light and is therefore a so-called broadband UV filter. Oxybenzone can be applied in sunscreen compositions or daily care cosmetics in an amount of from 1% to 6%. Further, it is sold under the trade names Eusolex 4360, Escalol 567 and Neo-Helipan BB.

Ethylhexyl-2-cyano-3,3-diphenyl-acrylate (INCI octocrylene) is an oil soluble organic UV-B filter with an absorption maximum at 302 nm. It provides a broad UV-B absorbance for balanced UV protection and is known to be an efficient stabilizer for photo-unstable UV filters. Octocrylene is sold by BASF under the tradename Uvinul® N 539 T.

2-Ethylhexyl-(2E)-3-(4-methoxyphenyl)acrylate (INCI ethylhexyl methoxy cinnamate) is an odorless and colorless UV-B filter with an absorption maximum at 310 nm. It is a good solvent for other crystalline UV filters. Ethylhexyl methoxy cinnamate is sold under the tradename Uvinul® MC 80 by BASF.

Isoamyl-4-methoxycinnamate (INCI isoamyl-p-methoxy cinnamate) is an oil soluble organic UV-B filter. It absorbs UV-B light in the region of from 280 nm to 320 nm. It can be applied in sunscreen compositions or daily care cosmetics in a maximum concentration of 10%.

2,2'-methylene bis[6-(2H-benzotriazol-2-yl)-4-(1,1,3,3-tetramethylbutyl)phenol] (INCI methylene bis-benzotriazolyl tetramethylbutylphenol) is a broadband UV filter, which absorbs UV-B light as well as UV-A light. Furthermore, it is a hybrid UV filter, which absorbs UV light as an organic compound, but also scatters some of the light, since it is a particulate UV filter, which is typically present in the form of micro fine organic particles. Methylene-bis-benzotriazolyl tetramethylbutylphenol (also referred to as MBBT) is a UV filter belonging to the group of benzotriazole derivatives. It is sold under the tradename Tinosorb® M by BASF.

2,4,6-Tris(biphenyl-4-yl)-1,3,5-triazine (INCI tris-biphenyl triazine), also referred to as TBPT, is a particulate organic UV filter belonging to the group of triazine derivatives. It is sold under the tradename Tinosorb® A2B by BASF. It provides protection in the UV-AII and UV-B range with an absorption maximum at 310 nm.

2,4-Bis-{[4-(2-ethyl-hexyloxy)-2-hydroxy]-phenyl}-6-(4-methoxyphenyl)-1,3,5-triazine (INCI bis-ethylhexyloxyphenol methoxyphenyl triazine), also referred to as BEMT is an UV filter belonging to the group of triazine derivatives. It is sold under the tradename Tinosorb S by BASF. It is a broad spectrum UV filter. BEMT can be either provided as an oil soluble UV filter or dissolved in a polyacrylate matrix to be dispersible in water. In the latter case, it is referred to as Tinosorb® S Aqua or Tinosorb S Lite Aqua.

The term "alkyl" as used herein denotes in each case a straight-chain or branched alkyl group having usually from 1 to 10 carbon atoms, preferably from 1 to 6 carbon atoms, even more preferably from 1 to 4 carbon atoms. Exemplified alkyl groups include methyl, ethyl, n-propyl, iso-propyl, n-butyl, 2-butyl, iso-butyl, tert.-butyl, n-pentyl, 1-methylbutyl, 2-methylbutyl, 3-methylbutyl, and 2,2-dimethylpropyl. Methyl, ethyl, n-propyl and iso-propyl are particularly preferred.

The term "dispersible in" as used herein indicates that a certain compound is not soluble in the respective water or oil phase, but finely dispersed in the respective phase.

The term "polymer matrix" as used herein is directed to matrices, which consist of multiple polymer chains grouped in a way to entrap, enclose or also dissolve molecules, such as different organic compounds.

The term "paraben" refers to a class of preservatives used in cosmetic and pharmaceutical compositions. They are commonly used due to their bactericidal and fungicidal properties. The chemical structure of parabens is based on parahydroxybenzoates or esters of parahydroxybenzoic acid, e.g. methylparaben, ethylparaben, propylparaben, butylparaben or heptylparaben.

The term "emollient" relates to cosmetic preparations used for protecting, moisturizing and lubricating the skin. The word emollient is derived from the Latin word mollire, to soften. In general, emollients prevent evaporation of water from the skin by forming an occlusive coating. They can be divided into different groups depending on their polarity index.

The term "polarity index" refers to non-polar or polar oils. Non-polar oils are mainly based on hydrocarbons and lack an electronegative element, such as oxygen. In contrast, polar oils contain heteroatoms that differ in electronegativity, which results in a dipole moment. However, such oils are still insoluble in water, i.e. hydrophob. The polarity index can be determined by measuring the interfacial tension between the respective oil and water.

The term "$C_{12}$-$C_{15}$ alkyl benzoate" refers to esters of benzoic acid with fatty alcohols containing a $C_{12}$-$C_{15}$-alkyl chain. $C_{12}$-$C_{15}$ alkyl chain is defined as an alkyl chain with $C_{12}$, $C_{13}$, $C_{14}$ or $C_{15}$ chain length.

The definition of "broadband" protection (also referred to as broad-spectrum or broad protection) is based on the "critical wavelength". For broadband coverage, UV-B and UV-A protection must be provided. According to the US requirements, a critical wavelength of at least 370 nm is required for achieving broad spectrum protection. Furthermore, it is recommended by the European Commission that all sunscreen or cosmetic compositions should have an UVA protection factor, which is at least one third of the labelled sun protection factor (SPF), e.g. if the sunscreen composition has an SPF of 30 the UVA protection factor has to be at least 10.

Preferred embodiments regarding the sunscreen or daily care composition according to the present invention are described hereinafter. It is to be understood that the preferred embodiments of the invention are preferred alone or in combination with each other.

As indicated above, the present invention relates in one embodiment to a sunscreen or daily care composition comprising (i) hexyl 2-[4-(diethylamino)-2-hydroxybenzoyl]benzoate (INCI diethylamino hydroxybenzoyl hexyl benzoate); and (ii) 1-(4-(1,1-dimethylethyl)phenyl)-3-(4-methoxyphenyl)propane-1,3-dione (INCI butyl methoxydibenzoylmethane); and (iii) at least one organic particulate UV filter;

wherein the composition does not comprise 2-hydroxy-4-methoxybenzophenone (INCI oxybenzone) and ethylhexyl-2-cyano-3,3-diphenyl-acrylate (INCI octocrylene).

In a second embodiment, the present invention relates to a sunscreen or daily care composition comprising (i) hexyl 2-[4-(diethylamino)-2-hydroxybenzoyl]benzoate (INCI diethylamino hydroxybenzoyl hexyl benzoate) in an amount of from 1% to 9% by weight, based on the total weight of the composition; and (ii) 1-(4-(1,1-dimethylethyl)phenyl)-3-(4-methoxyphenyl)propane-1,3-dione (INCI butyl methoxydibenzoylmethane); and (iii) at least one organic particulate UV filter; and (iv) at least one emollient with a polarity index of <30 mN/m wherein the composition does not comprise 2-hydroxy-4-methoxybenzophenone (INCI oxybenzone), ethylhexyl-2-cyano-3,3-diphenyl-acrylate (INCI octocrylene) and benzylidene malonates according to the following preferred structures:

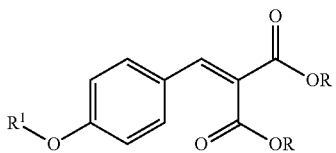

wherein
R¹ is methyl, ethyl, propyl or n-butyl;
if R¹ is methyl, then
R is tert. butyl or a radical of formula

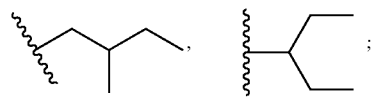

or a radical of formula

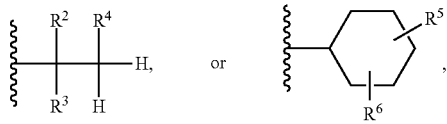

wherein
R² and R³ are independently from each other hydrogen or methyl;
R⁴ is methyl, ethyl or n-propyl;
R⁵ and R⁶ are independently from each other hydrogen or $C_1$-$C_3$-alkyl;
if R¹ is ethyl, propyl or n-butyl, then
R is isopropyl.

In connection with the present invention, in particular with regard to the first and second embodiment, the following preferences regarding the sunscreen composition are relevant.

In one embodiment of the present invention, the sunscreen or daily care composition comprises
(i) hexyl 2-[4-(diethylamino)-2-hydroxybenzoyl]benzoate (INCI diethylamino hydroxybenzoyl hexyl benzoate); and
(ii) 1-(4-(1,1-dimethylethyl)phenyl)-3-(4-methoxyphenyl)propane-1,3-dione (INCI butyl methoxydibenzoylmethane); and
(iii) at least one organic particulate UV filter;
wherein the composition does not comprise 2-hydroxy-4-methoxybenzophenone (INCI oxybenzone) and ethylhexyl-2-cyano-3,3-diphenyl-acrylate (INCI octocrylene).

In a preferred embodiment of the present invention, the sunscreen or daily care composition as defined above does not comprise benzylidene malonates according to the following preferred structures:

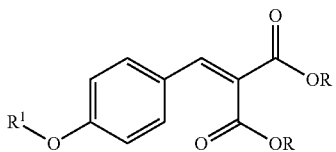

wherein
R¹ is methyl, ethyl, propyl or n-butyl;
if R¹ is methyl, then
R is tert. butyl or a radical of formula

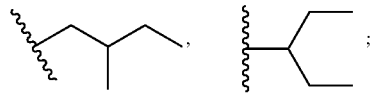

or a radical of formula

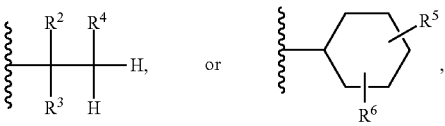

wherein
R² and R³ are independently from each other hydrogen or methyl;
R⁴ is methyl, ethyl or n-propyl;
R⁵ and R⁶ are independently from each other hydrogen or $C_1$-$C_3$-alkyl;
if R¹ is ethyl, propyl or n-butyl, then
R is isopropyl.

In another preferred embodiment of the present invention, the sunscreen or daily care composition as defined above does not comprise benzylidene malonates.

In another embodiment of the present invention, the sunscreen or daily care composition as defined above does not comprise 2-ethylhexyl-(2E)-3-(4-methoxyphenyl)acrylate (INCI ethylhexyl methoxy cinnamate) and isoamyl-4-methoxycinnamate (INCI isoamyl-p-methoxy cinnamate).

In yet another embodiment of the present invention, the sunscreen or daily care composition as defined above is free of parabens. In this connection, it is to be understood that parabens are also known by the synonyms parahydroxybenzoate, oxybenzoates, oxybenzoic acid, hydroxybenzoic acid, and hydroxybenzoate, which are also excluded from the sunscreen or daily care composition according to the present invention.

In yet another embodiment of the present invention, the sunscreen or daily care composition as defined above is free of phenoxyethanol.

In connection with the above embodiments, it is to be understood that free of means that the composition does not comprise the above-defined compounds or substances. In particular, it is to be understood that the composition does not comprise the above-defined compounds or substances in an amount of more than 0.8% by weight respectively, based on the total weight of the composition. Furthermore, it is to be understood that the composition does not comprise the above-defined compounds or substances in an amount of more than 0.5% by weight respectively.

In a preferred embodiment of the present invention, the sunscreen or daily care composition as defined above does not comprise the compounds or substances as defined above at all.

In connection with the above embodiments, it is to be understood that the sunscreen or daily care composition as defined above according to the present invention is free of the substances as defined above or the combinations as defined below.

Thus, in one preferred embodiment of the present invention, the sunscreen or daily care composition as defined above is further free of
- ethylhexyl methoxy cinnamate and isoamyl-p-methoxy cinnamate, and
- parabens.

In another preferred embodiment of the present invention, the sunscreen or daily care composition as defined above is further free of
- ethylhexyl methoxy cinnamate and isoamyl-p-methoxy cinnamate, and
- phenoxyethanol.

In yet another preferred embodiment of the present invention, the sunscreen or daily care composition as defined above is further free of
- parabens, and
- phenoxyethanol.

In yet another preferred embodiment of the present invention, the sunscreen or daily care composition as defined above is further free of
- ethylhexyl methoxy cinnamate and isoamyl-p-methoxy cinnamate,
- parabens, and
- phenoxyethanol.

In connection with the above preferred embodiments it is to be understood that the above substances or combination of substances are not enclosed in the sunscreen or daily care composition as defined above in addition to 2-hydroxy-4-methoxybenzophenone (INCI oxybenzone) and ethylhexyl-2-cyano-3,3-diphenyl-acrylate (INCI octocrylene).

In a particularly preferred embodiment of the present invention, the sunscreen or daily care composition does not comprise 2-hydroxy-4-methoxybenzophenone (INCI oxybenzone), ethylhexyl-2-cyano-3,3-diphenyl-acrylate (INCI octocrylene) and benzylidene malonates as defined above.

Further, in connection with the above preferred embodiments, it is to be understood that free of means that the composition does not comprise the substances or combinations as defined above. In particular, it is to be understood that the composition does not comprise the above-defined substances or combinations thereof in an overall amount of more than 0.8% by weight, based on the total weight of the composition. Furthermore, it is to be understood that the composition does not comprise the above-defined substances or combinations thereof in an overall amount of more than 0.5% by weight.

In a preferred embodiment of the present invention, the sunscreen or daily care composition does not comprise the above-defined substances or combinations thereof at all.

In one embodiment of the present invention, the sunscreen or daily care composition as defined above further comprises at least one emollient with a polarity index of <30 mN/m.

In a preferred embodiment of the present invention, the sunscreen or daily care composition as defined above further comprises at least one emollient with a polarity index of <30 mN/m selected from
- esters of linear or branched fatty acids with linear or branched fatty alcohols;
- esters of aromatic carboxylic acids with linear or branched fatty alcohols;
- di- and tricarboxylic acid esters with linear or branched alcohols;
- esters of hydroxycarboxylic acids with linear or branched fatty alcohols;
- esters of linear or branched fatty acids with polyhydric alcohol;
- mono-, di-, tri-glycerides based on $C_6$-$C_{18}$ fatty acids;
- guerbet alcohols.

In a more preferred embodiment of the present invention, the sunscreen or daily care composition as defined above further comprises at least one emollient with a polarity index of <30 mN/m selected from the group consisting of $C_{12}$-$C_{15}$ alkyl benzoate, caprylic/capric triglyceride, butylene glycol dicaprylate/dicaprate, propylene glycol dicaprylate/dicaprate, diisopropyl sebacate, octyldodecanol, isopropyl palmitate, isopropyl myristate, dicaprylyl carbonate, phenethyl benzoate, dibutyl adipate, diisopropyl adipate, triethyl citrate and tributyl citrate.

In a preferred embodiment, the sunscreen or daily care composition comprises the at least one emollient in an amount of from 1% to 20% by weight, preferably in an amount of from 2% to 15% by weight, based on the total weight of the sunscreen or daily care composition. It is to be understood that these amounts refer to each individual emollient in the sunscreen or daily care composition. Thus, each individual emollient in the sunscreen or daily care composition is preferably present in an amount of from 1% to 20% by weight, preferably in an amount of from 2% to 15% by weight, based on the total weight of the sunscreen or daily care composition. If two or more emollients are present in the sunscreen or daily care composition, the overall amount of emollients may preferably be in the range of from 1% to 35% by weight, preferably from 2% to 25% by weight, based on the total weight of the sunscreen or daily care composition.

In connection with the above preferred embodiments regarding the addition of the at least one emollient with a polarity index of <30 mN/m, it has surprisingly been found by the inventors of the present invention that the addition of at least one emollient as defined above enhances the solubility properties and performance of the UV filters as defined above in an octocrylene free sunscreen or daily care composition. In this connection, it is to be understood that the wavelength of maximum absorbance (λmax) is an indicator to describe the performance of a UV filter molecule. It gives the wavelength at which the absorbance is at maximum.

In connection with the present invention, in particular with regard to the first and second embodiment, the following preferences regarding the UV filters are relevant in connection with the above listed embodiments of the invention.

In one embodiment of the present invention, the sunscreen or daily care composition as defined above comprises
 (i) hexyl 2-[4-(diethylamino)-2-hydroxybenzoyl]benzoate (INCI diethylamino hydroxybenzoyl hexyl benzoate); and
 (ii) 1-(4-(1,1-dimethylethyl)phenyl)-3-(4-methoxyphenyl)propane-1,3-dione (INCI butyl methoxydibenzoylmethane); and
 (iii) at least one organic particulate UV filter;
wherein the composition does not comprise 2-hydroxy-4-methoxybenzophenone (INCI oxybenzone) and ethylhexyl-2-cyano-3,3-diphenyl-acrylate (INCI octocrylene).

In a second embodiment, the present invention relates to a sunscreen or daily care composition comprising
 (i) hexyl 2-[4-(diethylamino)-2-hydroxybenzoyl]benzoate (INCI diethylamino hydroxybenzoyl hexyl benzoate) in an amount of from 1% to 9% by weight, based on the total weight of the composition; and
 (ii) 1-(4-(1,1-dimethylethyl)phenyl)-3-(4-methoxyphenyl)propane-1,3-dione (INCI butyl methoxydibenzoylmethane); and (iii) at least one organic particulate UV filter; and
(iv) at least one emollient with a polarity index of <30 mN/m wherein the composition does not comprise 2-hydroxy-4-methoxybenzophenone (INCI oxybenzone), ethylhexyl-2-cyano-3,3-diphenyl-acrylate (INCI octocrylene) and benzylidene malonates according to the following preferred structures:

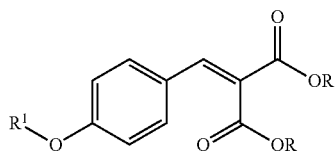

wherein
$R^1$ is methyl, ethyl, propyl or n-butyl;
if $R^1$ is methyl, then
R is tert. butyl or a radical of formula

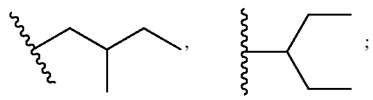

or a radical of formula

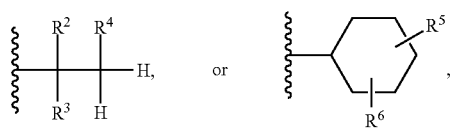

wherein
$R^2$ and $R^3$ are independently from each other hydrogen or methyl;
$R^4$ is methyl, ethyl or n-propyl;
$R^5$ and $R^6$ are independently from each other hydrogen or $C_1$-$C_3$-alkyl;
if $R^1$ is ethyl, propyl or n-butyl, then
R is isopropyl.

In a preferred embodiment of the present invention, the sunscreen or daily care composition as defined above comprises the at least one organic particulate UV filter, wherein "at least one organic particulate UV filter" may preferably refer to from 1 to 4 organic particulate UV filter. In a more preferred embodiment the "at least one organic particulate UV filter" may preferably refer to from 1 to 3 organic particulate UV filter.

In another preferred embodiment of the present invention, the sunscreen or daily care composition as defined above comprises the at least one organic particulate UV filter selected from the group consisting of 2,2'-methylene bis[6-(2H-benzotriazol-2-yl)-4-(1,1,3,3-tetramethylbutyl)phenol] (INCI methylene bis-benzotriazolyl tetramethylbutylphenol), 2,4,6-tris(biphenyl-4-yl)-1,3,5-triazine (INCI trisbiphenyl triazine), 1,1'-(1,4-piperazinediyl)bis[1-[2-[4-(diethylamino)-2-hydroxybenzoyl]phenyl]-methanone (INCI bis-(diethylaminohydroxybenzoyl benzoyl) piperazine), 5,6,5',6'-tetraphenyl-3-3'-(1,4-phenylene)bis(1,2,4-triazine) (INCI phenylene bis-diphenyltriazine), micronized 1,4-di(benzoxazole-2'-yl)benzene and combinations thereof.

In a more preferred embodiment of the present invention, the sunscreen or daily care composition as defined above comprises the at least one organic particulate UV filter selected from the group consisting of 2,2'-methylene bis[6-(2H-benzotriazol-2-yl)-4-(1,1,3,3-tetramethylbutyl)phenol] (INCI methylene bis-benzotriazolyl tetramethylbutylphenol), 2,4,6-tris(biphenyl-4-yl)-1,3,5-triazine (INCI trisbiphenyl triazine), 5,6,5',6'-tetraphenyl-3-3'-(1,4-phenylene) bis(1,2,4-triazine) (INCI phenylene bis-diphenyltriazine), and combinations thereof.

In a preferred embodiment of the present invention, the sunscreen or daily care composition as defined above comprises the at least one organic particulate UV filter an amount of from 0.5% to 10% by weight, based on the total weight of the composition. In a more preferred embodiment of the present invention, the sunscreen or daily care composition comprises the at least one organic particulate UV filter in an amount of from 1% to 8% by weight, based on the total weight of the composition. It is to be understood that these amounts refer to each individual organic particulate UV filter in the sunscreen or daily care composition. Thus, each individual organic particulate UV filter in the sunscreen or daily care composition is preferably present in an amount of from 0.5% to 10% by weight, preferably in an amount of from 1% to 8% by weight, based on the total weight of the sunscreen or daily care composition. If two or more organic particulate UV filters are present in the sunscreen or daily care composition, the overall amount of organic particulate UV filters may preferably be in the range of from 1% to 30% by weight, preferably from 3% to 30% by weight, based on the total weight of the sunscreen or daily care composition.

In connection with the above preferred embodiments, it is to be understood that the at least one organic particulate UV filter as defined above, is present in the sunscreen or daily care composition in addition to hexyl 2-[4-(diethylamino)-2-hydroxybenzoyl]benzoate (INCI diethylamino hydroxybenzoyl hexyl benzoate) and 1-(4-(1,1-dimethylethyl)phenyl)-3-(4-methoxyphenyl)propane-1,3-dione (INCI butyl methoxydibenzoylmethane).

Thus, in a preferred embodiment of the present invention, the sunscreen or daily care composition comprises hexyl 2-[4-(diethylamino)-2-hydroxybenzoyl]benzoate (INCI diethylamino hydroxybenzoyl hexyl benzoate) in an amount of from 1% to 10% by weight, based on the total weight of the composition. In another preferred embodiment of the present invention, the sunscreen or daily care composition comprises hexyl 2-[4-(diethylamino)-2-hydroxybenzoyl]benzoate (INCI diethylamino hydroxybenzoyl hexyl benzoate) in an amount of from 1% to 9% by weight, based on the total weight of the composition. In a more preferred embodiment of the present invention, the sunscreen or daily care composition comprises hexyl 2-[4-(diethylamino)-2-hydroxybenzoyl]benzoate (INCI diethylamino hydroxybenzoyl hexyl benzoate) in an amount of from 1% to 8% by weight, based on the total weight of the composition. In another more preferred embodiment of the present invention, the sunscreen or daily care composition comprises hexyl 2-[4-(diethylamino)-2-hydroxybenzoyl]benzoate (INCI diethylamino hydroxybenzoyl hexyl benzoate) in an amount of from 2% to 8% by weight, preferably in an amount of from 4% to 6% by weight based on the total weight of the composition.

In another preferred embodiment of the present invention, the sunscreen or daily care composition comprises 1-(4-(1,1-dimethylethyl)phenyl)-3-(4-methoxyphenyl)propane-1,3- dione (INCI butyl methoxydibenzoylmethane) in an amount of from 1% to 5% by weight, based on the total weight of the composition.

As indicated above, it is preferred that the sunscreen or daily care composition comprises diethylamino hydroxybenzoyl hexyl benzoate and butyl methoxydibenzoylmethane and at least one organic particulate UV filter. Further, it is preferred that the sunscreen or daily care composition as defined above comprises 2 or more organic particulate UV filter. In particular, it is preferred that the sunscreen or daily care composition comprises from 1 to 3 organic particulate UV filter.

If the sunscreen or daily care composition as defined above comprises from 1 to 4 organic particulate UV filter the following combinations of the 1 to 4 organic particulate UV filter with diethylamino hydroxybenzoyl hexyl benzoate and butyl methoxydibenzoylmethane are part of the invention.

If the sunscreen or daily care composition comprises 1 organic particulate UV filter the following combinations with diethylamino hydroxybenzoyl hexyl benzoate and butyl methoxydibenzoylmethane are further part of the invention In one preferred embodiment of the present invention, the sunscreen or daily care composition comprises diethylamino hydroxybenzoyl hexyl benzoate and butyl methoxydibenzoylmethane and methylene bis-benzotriazolyl tetramethylbutylphenol.

In another preferred embodiment of the present invention, the sunscreen or daily care composition comprises diethylamino hydroxybenzoyl hexyl benzoate and butyl methoxydibenzoylmethane and trisbiphenyl triazine.

In yet another preferred embodiment of the present invention, the sunscreen or daily care composition comprises diethylamino hydroxybenzoyl hexyl benzoate and butyl methoxydibenzoylmethane and phenylene bis-diphenyltriazine.

In yet another preferred embodiment of the present invention, the sunscreen or daily care composition comprises diethylamino hydroxybenzoyl hexyl benzoate and butyl methoxydibenzoylmethane and bis-(diethylaminohydroxybenzoyl benzoyl) piperazine.

If the sunscreen or daily care composition comprises 2 organic particulate UV filter the following combinations with diethylamino hydroxybenzoyl hexyl benzoate and butyl methoxydibenzoylmethane are further part of the invention.

In one preferred embodiment of the present invention, the sunscreen or daily care composition comprises diethylamino hydroxybenzoyl hexyl benzoate, butyl methoxydibenzoylmethane, methylene bis-benzotriazolyl tetramethylbutylphenol and trisbiphenyl triazine.

In another preferred embodiment of the present invention, the sunscreen or daily care composition comprises diethylamino hydroxybenzoyl hexyl benzoate, butyl methoxydibenzoylmethane, methylene bis-benzotriazolyl tetramethylbutylphenol and phenylene bis-diphenyltriazine.

In yet another preferred embodiment of the present invention, the sunscreen or daily care composition comprises diethylamino hydroxybenzoyl hexyl benzoate, butyl methoxydibenzoylmethane, methylene bis-benzotriazolyl tetramethylbutylphenol and bis-(diethylaminohydroxybenzoyl benzoyl) piperazine.

In yet another preferred embodiment of the present invention, the sunscreen or daily care composition comprises diethylamino hydroxybenzoyl hexyl benzoate, butyl methoxydibenzoylmethane, trisbiphenyl triazine and phenylene bis-diphenyltriazine.

In yet another preferred embodiment of the present invention, the sunscreen or daily care composition comprises diethylamino hydroxybenzoyl hexyl benzoate, butyl methoxydibenzoylmethane, trisbiphenyl triazine and bis-(diethylaminohydroxybenzoyl benzoyl) piperazine.

In yet another preferred embodiment of the present invention, the sunscreen or daily care composition comprises diethylamino hydroxybenzoyl hexyl benzoate, butyl methoxydibenzoylmethane, phenylene bis-diphenyltriazine and bis-(diethylaminohydroxybenzoyl benzoyl) piperazine.

If the sunscreen or daily composition comprises 3 organic particulate UV filter the following combinations with diethylamino hydroxybenzoyl hexyl benzoate and butyl methoxydibenzoylmethane are further part of the invention.

In one preferred embodiment, the sunscreen or daily care composition comprises diethylamino hydroxybenzoyl hexyl benzoate, butyl methoxydibenzoylmethane, methylene bis-benzotriazolyl tetramethylbutylphenol, trisbiphenyl triazine and phenylene bis-diphenyltriazine.

In another preferred embodiment, the sunscreen or daily care composition comprises diethylamino hydroxybenzoyl hexyl benzoate, butyl methoxydibenzoylmethane, methylene bis-benzotriazolyl tetramethylbutylphenol, trisbiphenyl triazine and bis-(diethylaminohydroxybenzoyl benzoyl) piperazine.

In yet another preferred embodiment, the sunscreen or daily care composition comprises diethylamino hydroxybenzoyl hexyl benzoate, butyl methoxydibenzoylmethane, methylene bis-benzotriazolyl tetramethylbutylphenol, phenylene bis-diphenyltriazine and bis-(diethylaminohydroxybenzoyl benzoyl) piperazine.

In yet another preferred embodiment, the sunscreen or daily care composition comprises diethylamino hydroxybenzoyl hexyl benzoate, butyl methoxydibenzoylmethane, trisbiphenyl triazine, phenylene bis-diphenyltriazine and bis-(diethylaminohydroxybenzoyl benzoyl) piperazine.

If the sunscreen or daily care composition comprises 4 organic particulate UV filter the following combinations with diethylamino hydroxybenzoyl hexyl benzoate and butyl methoxydibenzoylmethane are further part of the invention.

In one preferred embodiment, the sunscreen or daily care composition comprises diethylamino hydroxybenzoyl hexyl benzoate, butyl methoxydibenzoylmethane, methylene bis-benzotriazolyl tetramethylbutylphenol, trisbiphenyl triazine, phenylene bis-diphenyltriazine and bis-(diethylaminohydroxybenzoyl benzoyl) piperazine.

In a preferred embodiment of the present invention, the sunscreen or daily care composition as defined above further comprises at least one UV filter selected from 4,4',4"-(1,3,5-triazine-2,4,6-triyltriimino)tris-benzoic acid-tris(2-ethylhexyl)ester (INCI ethylhexyl triazone), 4,4'-[[6-[[4-[[(1,1-dimethylethyl)amino]carbonyl]phenyl]amino]-1,3,5-triazin-2,4-diyl]diimino]bis-benzoic acid-bis(2-ethylhexyl)ester (INCI diethylhexyl-butamidotriazone), 2,4-bis-{[4-(2-ethylhexyloxy)-2-hydroxy]-phenyl}-6-(4-methoxyphenyl)-1,3,5 triazine (INCI bis-ethylhexyloxyphenol methoxyphenyl triazine) and combinations thereof. In connection with the above preferred embodiment, it is to be understood that "at least one UV filter" may preferably refer to from 1 to 3 UV filter.

In a particularly preferred embodiment of the present invention, the sunscreen or daily care composition as defined above comprises
(i) hexyl 2-[4-(diethylamino)-2-hydroxybenzoyl]benzoate (INCI diethylamino hydroxybenzoyl hexyl benzoate); and (ii) 1-(4-(1,1-dimethylethyl)phenyl)-3-(4-methoxyphenyl)propane-1,3-dione (INCI butyl methoxydibenzoylmethane); and (iii) 2,2'-methylene bis[6-(2H-benzotriazol-2-yl)-4-(1,1,3,3-tetramethylbutyl)phenol] (INCI methylene bis-benzotriazolyl tetramethylbutylphenol);

wherein the composition does not comprise 2-hydroxy-4-methoxybenzophenone (INCI oxybenzone) and ethylhexyl-2-cyano-3,3-diphenyl-acrylate (INCI octocrylene).

In another particularly preferred embodiment of the present invention, the sunscreen or daily care composition as defined above comprises methylene bis-benzotriazolyl tetramethylbutylphenol and butyl methoxydibenzoylmethane in a ratio of 1:1.

In another particularly preferred embodiment of the present invention, the sunscreen or daily care composition as defined above comprises (i) hexyl 2-[4-(diethylamino)-2-hydroxybenzoyl]benzoate (INCI diethylamino hydroxybenzoyl hexyl benzoate, DHHB); and (ii) 1-(4-(1,1-dimethylethyl)phenyl)-3-(4-methoxyphenyl)propane-1,3-dione (INCI butyl methoxydibenzoylmethane, BMDBM); and (iii) 2,2'-methylene bis[6-(2H-benzotriazol-2-yl)-4-(1,1,3,3-tetramethylbutyl)phenol] (INCI methylene bis-benzotriazolyl tetramethylbutylphenol, MBBT);

wherein the composition does not comprise 2-hydroxy-4-methoxybenzophenone (INCI oxybenzone) and ethylhexyl-2-cyano-3,3-diphenyl-acrylate (INCI octocrylene) and wherein methylene bis-benzotriazolyl tetramethylbutylphenol and butyl methoxydibenzoylmethane are present in a ratio of 1:1.

In connection with the above preferred embodiments, it has surprisingly been found by the inventors of the present invention that in the specific combination with MBBT and DHHB, the UV filter BMDBM is photostabilized. A skilled person is aware, that BMDBM is a frequently used UV absorber, which tends to isomerize under radiation to build a diketone in the triplet state. This diketone is very likely to undergo photolysis leading to a degradation of BMDBM. Therefore, stabilizing agents need to be added to compositions comprising BMDBM, for example photo stable UV absorber such as octocrylene are commonly used. Thus, it has been a surprising finding by the inventors of the present invention, that BMDBM can be stabilized in an octocrylene free sunscreen composition by DHHB and MBBT, wherein none of the stabilizing UV filters has to be used in an excess amount.

In connection with the above particularly preferred embodiments, it is to be understood that the sunscreen or daily care composition as defined above comprises hexyl 2-[4-(diethylamino)-2-hydroxybenzoyl]benzoate (INCI diethylamino hydroxybenzoyl hexyl benzoate) in an amount of from 1% to 8% by weight, based on the total weight of the composition.

Further, it is to be understood that the sunscreen or daily care composition comprises 1-(4-(1,1-dimethylethyl)phenyl)-3-(4-methoxyphenyl)propane-1,3-dione (INCI butyl methoxydibenzoylmethane) in an amount of from 1% to 5% by weight, based on the total weight of the composition and 2,2'-methylene bis[6-(2H-benzotriazol-2-yl)-4-(1,1,3,3-tetramethylbutyl)phenol] (INCI methylene bis-benzotriazolyl tetramethylbutylphenol) in an amount of from 1% to 10% by weight, based on the total weight of the composition. As indicated above, methylene bis-benzotriazolyl tetramethylbutylphenol and butyl methoxydibenzoylmethane are preferably present in a ratio of 1:1 in the sunscreen or daily care composition as defined above. Depending on the ratio in which the two compounds as defined above are present, the amount of methylene bis-benzotriazolyl tetramethylbutylphenol is preferably of from 1% to 5% by weight and the amount of butyl methoxydibenzoylmethane is preferably of from 1% to 5% by weight, based on the total weight of the composition. In other words, this means that if methylene bis-benzotriazolyl tetramethylbutylphenol and butyl methoxydibenzoylmethane are for example present in a ratio of 1:1, methylene bis-benzotriazolyl tetramethylbutylphenol is present in an amount of e.g. 3% by weight and butyl methoxydibenzoylmethane is also present in an amount of e.g. 3% by weight.

In connection with the above preferred embodiments, it is to be understood that the total weight of the sunscreen or daily care composition refers to the sunscreen or daily care composition as defined above, wherein the sunscreen composition may comprise at least one additive.

In one embodiment, the at least one additive is selected from the group consisting of emulsifier, emollients, viscosity regulators (thickeners), sensory enhancers, adjuvants, preservatives, and combinations thereof.

Preferred emulsifiers include
- glucose derivatives such as cetearyl glucoside, arachidyl glucoside, lauryl glucoside, polyglyceryl-3 methylglucose distearate, methyl glucose sesquistearate;
- sucrose derivative such as sucrose polystearate, sucrose palmitate;
- sorbitol derivatives such as polysorbate-n, PEG-10 sorbitan laurate;
- fatty alcohol polyglycolethers and fatty acid polyglycolethers such as ceteareth-20, beheneth-25, steareth-2, PEG-100 stearate;
- glycerides of fatty acids such as glyceryl stearate, glyceryl oleate;
- glumatic acid derivatives such as sodium stearoyl glutamate;
- sulfosuccinic acid derivatives such as disodium cetearyl sulfosuccinate;
- phosphoric acid derivatives such as potassium cetyl phosphate;
- fatty acid esters of polyglyceryl such as polyglyceryl-3-diisostearate, polyglyceryl-2-dipolyhydroxystearate;
- oxyalkenylated organomodified silicone/polysiloxane/polyalkyl/polyether copolymers and derivatives.

Preferred emollients include
- esters of linear or branched fatty acids with linear or branched fatty alcohols such as propylheptyl caprylate, coco caprylate, isopropyl myristate, ethylhexyl palmitate;
- esters of aromatic carboxylic acids with linear or branched fatty alcohols such as $C_{12}$-$C_{15}$-alkyl benzoate, ethylhexyl benzoate, phenethyl benzoate;
- dicarboxylic acid esters with linear or branched alcohols such as dibutyl adipate, dicaprylyl carbonate, diisopropyl sebacate;
- esters of hydroxycarboxylic acids with linear or branched fatty alcohols;
- esters of linear or branched fatty acids with polyhydric alcohol such as butylene glycol dicaprylate/dicaprate;
- mono-, di-, tri-glycerides based on $C_6$-$C_{18}$ fatty acids such as caprylic/capric triglycerides, coco glycerides;
- guerbet alcohols such as octyldodecynol;
- hydrocarbons such as hydrogenated polyisobutene, mineral oil, squalene, isohexadecane;
- ethers such as dicaprylyl ether;

silicone derivatives (organomodified polysiloxanes) such as dimethylpolysiloxane, cyclic silicones.

Preferred thickeners include
fatty alcohols such as cetyl alcohol, cetearyl alcohol, stearyl alcohol;
fatty acids such as stearic acid;
fatty acid esters such as myristyl stearate;
waxes such as beeswax, carnauba wax, microcrystalline wax, ceresin, ozocerite;
polysaccharides or derivatives such as xanthan gum, guar gum, agar gum, alginates, gellan gum, carraghenan;
polyacrylates or homopolymers of reticulated acrylic acids or polyacrylamides such as carbomers, acrylate copolymers, acrylate/$C_{10}$-$C_{30}$-alkyl acrylate crosspolymer, acrylate/beheneth-25 methacrylate copolymer;
silicate derivatives such as magnesium silicates;
cellulose derivatives such as hydroxypropyl cellulose.

Preferred sensory enhancers include
polyamide derivatives such as nylon-12;
polymethyl methacrylates;
silica;
mica;
polymethylsilsesquioxane;
polyethylene;
starch derivatives such as aluminum starch octenylsuccinate;
dimethicone derivatives;
boron nitride;
HDI/trimethylol hexyllactone crosspolymer.

Preferred adjuvants include
tocopherol derivatives;
retinol derivatives;
ascorbic acid derivatives;
bisabolol;
allantoin;
panthenol;
chelating agents (EDTA, EDDS, EGTA, phytic acid, piroctone olamine);
ethylhexyl glycerin;
caprylyl glycol;
hydroxyacetophenone;
caprylhydroxymic acid;
propellants such as propane, butane, isobutene, dimethyl ether;
styrene/PVP or styrene acrylamide copolymers;
insect repellants such as butylacetylaminopropionate.

Preferred preservatives include
benzyl alcohol;
zingerone.

In another embodiment of the present invention, the sunscreen or daily care composition comprises at least one perfume.

Preferred perfumes are selected from the group consisting of limonene, citral, linalool, alpha-isomethylionon, geraniol, citronellol, 2-isobutyl-4-hydroxy-4-methyltetrahydropyrane, 2-tert.-pentylcyclohexylacetate, 3-methyl-5-phenyl-1-pentanol, 7-acetyl-1,1,3,4,4,6-hexamethyltetraline, adipine acid diester, alpha-amylcinnamaldehyde, alpha-methylionon, amyl C butylphenylmethylpropionalcinnamal, amylsalicylate, amylcinnamylalcohol, anisalcohol, benzoin, benzylalcohol, benzylbenzoate, benzylcinnamate, benzylsalicylate, bergamot oil, bitter orange oil, butylphenylmethylpropioal, cardamom oil, cedrol, cinnamal, cinnamylalcohol, citronnellylmethylcrotonate, lemon oil, coumarin, diethylsuccinate, ethyllinalool, eugenol, evernia furfuracea extracte, evernia prunastri extracte, farensol, guajak wood oil, hexylcinnamal, hexylsalicylate, hydroxycitronellal, lavender oil, lemon oil, linaylacetate, mandarine oil, menthyl PCA, methylheptenone, nutmeg oil, rosemary oil, sweet orange oil, terpineol, tonka bean oil, triethylcitrate, vanillin and combinations thereof.

In connection with the above preferred embodiments, it is to be understood that if the sunscreen or daily care composition comprises two or more additives, combinations of the additives as defined above are also part of the invention.

In connection with the at least one perfume present in the sunscreen or daily care composition, it has surprisingly been found that in case the composition comprises a UV filter in combination with a perfume, oxidative degeneration is reduced. In particular, it has surprisingly been found that the UV filter DHHB used alone or in combination with BMDBM in the presence of at least one perfume reduces the oxidative degeneration.

In connection with the above preferred and particularly preferred embodiments, it is to be understood that the sunscreen or daily care composition, in its final formulation, may exist in a wide variety of presentation forms, which include
liquid preparations as a W/O, O/W, O/W/O, W/O/W or PIT emulsion and all kinds of micro emulsions;
gels;
oil, cream, milk or lotion;
powder, a lacquer, a tablet or make-up;
sticks;
sprays (spray with propellant gas or pump-action spray) or an aerosol;
foams;
pastes.

In a further aspect, the present invention relates to the use of hexyl 2-[4-(diethylamino)-2-hydroxybenzoyl]benzoate (INCI diethylamino hydroxybenzoyl hexyl benzoate) and at least one organic particulate UV filter for photostabilizing 1-(4-(1,1-dimethylethyl)phenyl)-3-(4-methoxyphenyl)propane-1,3-dione (INCI butyl methoxydibenzoylmethane, BMDBM) in a sunscreen or daily care composition, wherein the composition does not comprise 2-hydroxy-4-methoxybenzophenone (INCI oxybenzone) and ethylhexyl-2-cyano-3,3-diphenyl-acrylate (INCI octocrylene).

In connection with the above further aspect it is to be understood that the sunscreen or daily care composition is as defined above according to the first and second embodiment. In particular, it is to be understood that the sunscreen or daily care composition is as defined above according to the first embodiment of the present invention.

Furthermore, it is to be understood that a skilled person is aware, that BMDBM is a frequently used UV absorber, which tends to isomerize under radiation to build a diketone in the triplet state. This diketone is very likely to undergo photolysis leading to a degradation of BMDBM. Therefore, stabilizing agents need to be added to compositions comprising BMDBM, for example UV absorber such as octocrylene are commonly used. Therefore, the UV filter BMDBM is stabilized in the sunscreen or daily care composition according to the present invention in the absence of the UV absorber octocrylene by the UV filter diethylamino hydroxybenzoyl hexyl benzoate and at least one organic particulate UV filter.

The present invention is further illustrated by the following examples.

EXAMPLES

Process of Manufacture of Sunscreen Compositions

The ingredients of part A, as well as the ingredients of part B as provided below in Table 1 for each tested sunscreen composition were combined and heated to 80° C. respectively, wherein part A was added to part B under stirring and was further homogenized. Subsequently, the sunscreen composition was cooled down to room temperature under stirring and the pH of each composition was adjusted to 6.5-7.00 with NaOH.

All amounts referred to in the following tables refer to the respective amounts in % by weight, based on the total weight of the composition.

Sunscreen Compositions

TABLE 1

| Ingredient (Trade Name) | Comparative composition 1a | Comparative composition 1b | Composition 1 |
|---|---|---|---|
| Part A | | | |
| Dibutyl adipate (Cetiol B) | 10.00 | 10.00 | 10.00 |
| $C_{12}$-$C_{15}$ alkyl benzoate (Cetiol AB) | 10.00 | 10.00 | 10.00 |
| Stearyl alcohol (Lanette 18) | 2.50 | 2.50 | 2.50 |
| BMDBM | 5.00 | 5.00 | 5.00 |
| DHHB (Uvinul A Plus) | 3.00 | 3.00 | 3.00 |
| OCR (Uvinul N539T) | 5.00 | — | — |
| Part B | | | |
| Water | qsp 100% | qsp 100% | qsp 100% |
| Glycerin | 2.00 | 2.00 | 2.00 |
| Disodium EDTA | 0.20 | 0.20 | 0.20 |
| Acrylates/Beheneth-25 methacrylate copolymer (Tinovis GTC) | 2.00 | 2.00 | 2.00 |
| Xanthan Gum (Rheocare XGN) | 0.50 | 0.50 | 0.50 |
| Part C | | | |
| MBBT (Tinosorb M)* | — | — | 5.00 |

*The amount refers to active matter, 5% MBBT corresponds to 10% of the commercial product Tinosorb M.

Recovery Measurements on Photo Stability of BMDBM

The comparative compositions 1a and 1b, and composition 1 are applied on roughened quartz plates (2 μl/cm²). Plates are irradiated using Atlas CPS device at different duration times:
 0 h (0 MED, no irradiation)
 1 h (5 MED),
 2 h (10 MED),
 4 h (24 MED).

In total, four plates are prepared for each irradiation condition. After irradiation, each plate is rinsed off with tetrahydrofuran. The rinsing solution is further analyzed via HPLC to determine the recovery of BMDBM.

TABLE 2

| | Comparative composition 1a | Comparative composition 1b | Composition 1 |
|---|---|---|---|
| 0 MED | 100% | 100% | 100% |
| 5 MED | 92% | 63% | 65% |
| 10 MED | 83% | 28% | 44% |
| 20 MED | 64% | 5% | 18% |

MED (Minimal Erythema Dose)

Measurement of Interfacial Tension (Polarity Index)

Interfacial tension of the respective emollients as listed below was measured using a Tensimat Densimat TD2000.

TABLE 3.1

| | | polarity index [mN/m] |
|---|---|---|
| polarity index >30 mN/m (reference emollients) | hydrogenated polyisobutene | 45 |
| | mineral oil | 43 |
| | cyclopentasiloxane | 32 |
| polarity index <30 mN/m | octyldodecanol | 25 |
| | butylene glycol dicaprylate/dicaprate | 22 |
| | C12-15 alkyl benzoate | 22 |
| | caprylic capric triglyceride | 21 |
| | propylene glycol dicaprylate/dicaprate | 20 |
| | diisopropyl sebacate | 19 |
| | phenethyl benzoate | 19 |
| | dibutyl adipate | 14 |
| | diisopropyl adipate | 12 |
| | triethyl citrate | 7 |
| | tributyl citrate | 10 |

UV Filter Performance

The wavelength of maximum absorbance (λmax) is an indicator to describe the performance of a UV filter molecule. It gives the wavelength at which the absorbance is at maximum. For a UVA filter, the wavelength of maximum absorbance should be close to 359 nm that corresponds to the apex of the PPD (persistent pigment darkening) effectiveness spectrum. The PPD effectiveness spectrum corresponds to the multiplication of the PPD (persistent pigment darkening) action spectrum with the light intensity (see ISO 24443).

The UV transmission spectrum of each UV filter-emollient mixture was measured from 290 to 400 nm using a UV/Vis spectrophotometer Perkin Elmer Lambda 25. Three stock solutions with a concentration of 1 mM of UV filter were prepared for each mixture. Further, three dilutions of each stock solution were prepared resulting in nine measurements in total per UV filter-emollient solution. Then, all solutions were filled in UV transparent quartz cuvette of 1 cm optical path-length for UV Transmission measurements.

λMax Values of BMDBM

TABLE 3.2

| | | λmax values [nm] (BMDBM) |
|---|---|---|
| polarity index >30 mN/m (reference emollients) | mineral oil | 355 |
| | hydrogenated polyisobutene | 354 |
| | cyclomethicone | 350 |
| polarity index <30 mN/m | diisopropyl adipate | 357 |
| | isopropyl myristate | 357 |
| | dicaprylyl carbonate | 357 |
| | dibutyl adipate | 358 |
| | caprylic capric triglyceride | 358 |
| | C12-15 alkyl benzoate | 359 |
| | phenethyl benzoate | 362 |
| | diisopropyl sebacate | 357 |

TABLE 3.2-continued

|  |  | λmax values [nm] (BMDBM) |
|---|---|---|
|  | octyldodecanol | 357 |
|  | triethyl citrate | 359 |
|  | tributyl citrate | 359 |

λMax Values of DHHB

TABLE 3.3

|  |  | λmax values [nm] (DHHB) |
|---|---|---|
| polarity index >30 mN/m (reference emollients) | hydrogenated polyisobutene | 345 |
|  | cyclomethicone | 345 |
|  | mineral oil | 346 |
| polarity index <30 mN/m | phenethyl benzoate | 355 |
|  | dibutyl adipate | 351 |
|  | C12-15 alkyl benzoate | 351 |
|  | diisopropyl adipate | 351 |
|  | butylene glycol dicaprylate/dicaprate | 350 |
|  | caprylic capric triglyceride | 350 |
|  | diisopropyl sebacate | 350 |
|  | octyldodecanol | 349 |
|  | triethyl citrate | 353 |
|  | tributyl citrate | 352 |

Solubility Measurements 0.02 g of UV Filter are added to 2 ml of the respective emollient as listed below, previously filled into a 20 ml vial with cap. The vial is placed in a thermostated water bath (25° C.) and the blend is stirred for seven days. If the tested UV-filter is fully soluble, additional filter is added until precipitation is observed. After seven days, the sample is centrifuged for 30 minutes at 13000 rpm. If the supernatant is turbid, it is filtered through a 0.2 µm non steril Membrex 25 PET filter. Prior to the measurement, the samples were either diluted with a suitable solvent, or, in case of lower concentrations measured without further dilution in quartz cuvettes of 1 cm optical path-length. The concentration of UV-filter is then determined with UV/Vis-spectroscopy using a Perkin Elmer Lambda 20 device (according to Method A in Herzog B., Giesinger J., Schnyder M., SOFW Journal, 2013, 139 (7), pages 7-14.).

TABLE 3.4

|  |  | solubility [%] (BMDBM) |
|---|---|---|
| polarity index >30 mN/m (reference emollients) | mineral oil | <1 |
|  | hydrogenated polyisobutene | <1 |
|  | cyclomethicone | <1 |
| polarity index <30 mN/m | diisopropyl adipate | 10 |
|  | dibutyl adipate | 18 |
|  | caprylic capric triglyceride | 12 |
|  | C12-15 alkyl benzoate | 14 |
|  | phenethyl benzoate | 25 |
|  | diisopropyl sebacate | 16 |
|  | octyldodecanol | 2 |
|  | triethyl citrate | 15 |
|  | tributyl citrate | 18 |

TABLE 3.5

|  |  | solubility [%] (DHHB) |
|---|---|---|
| polarity index >30 mN/m (reference emollients) | mineral oil | <1 |
|  | hydrogenated polyisobutene | <1 |
|  | cyclomethicone | <1 |
| polarity index <30 mN/m | phenethyl benzoate | 57 |
|  | dibutyl adipate | 31 |
|  | C12-15 alkyl benzoate | 22 |
|  | diisopropyl adipate | 21 |
|  | butylene glycol dicaprylate/dicaprate | 23 |
|  | propylene glycol dicaprylate/dicaprate | 22 |
|  | caprylic capric triglyceride | 14 |
|  | diisopropyl sebacate | 41 |
|  | octyldodecanol | 2.5 |
|  | triethyl citrate | 29.0 |
|  | tributyl citrate | 29.4 |

In a particularly preferred embodiment, the present invention refers to the following further items.

1. A sunscreen or daily care composition comprising
   (i) hexyl 2-[4-(diethylamino)-2-hydroxybenzoyl]benzoate (INCI diethylamino hydroxybenzoyl hexyl benzoate); and
   (ii) 1-(4-(1,1-dimethylethyl)phenyl)-3-(4-methoxyphenyl)propane-1,3-dione (INCI butyl methoxydibenzoylmethane); and
   (iii) at least one organic particulate UV filter;
wherein the composition does not comprise 2-hydroxy-4-methoxybenzophenone (INCI oxybenzone) and ethylhexyl-2-cyano-3,3-diphenyl-acrylate (INCI octocrylene).

2. The sunscreen or daily care composition according to item 1, wherein the composition does not comprise 2-ethylhexyl-(2E)-3-(4-methoxyphenyl)acrylate (INCI ethylhexyl methoxy cinnamate) and isoamyl-4-methoxycinnamate (INCI isoamyl-p-methoxy cinnamate).

3. The sunscreen or daily care composition according to item 1 or 2, wherein the composition is free of parabens.

4. The sunscreen or daily care composition according to any one of items 1 to 3, wherein the at least one organic particulate UV filter is selected from the group consisting of 2,2'-methylene bis[6-(2H-benzotriazol-2-yl)-4-(1,1,3,3-tetramethylbutyl)phenol] (INCI methylene bis-benzotriazolyl tetramethylbutylphenol), 2,4,6-tris(biphenyl-4-yl)-1,3,5-triazine (INCI trisbiphenyl triazine), 1,1'-(1,4-piperazinediyl)bis[1-[2-[4-(diethylamino)-2-hydroxybenzoyl]phenyl]-methanone (INCI bis-(diethylaminohydroxybenzoyl benzoyl) piperazine), 5,6,5',6'-tetraphenyl-3-3'-(1,4-phenylene)bis(1,2,4-triazine) (INCI phenylene bis-diphenyltriazine), micronized 1,4-di(benzoxazole-2'-yl)benzene and combinations thereof.

5. The sunscreen or daily care composition according to item 4, wherein the at least one organic particulate UV filter is selected from the group consisting of 2,2'-methylene bis[6-(2H-benzotriazol-2-yl)-4-(1,1,3,3-tetramethylbutyl)phenol] (INCI methylene bis-benzotriazolyl tetramethylbutylphenol), 2,4,6-tris(biphenyl-4-yl)-1,3,5-triazine (INCI trisbiphenyl triazine), 5,6,5',6'-tetraphenyl-3-3'-(1,4-phenylene)bis(1,2,4-triazine) (INCI phenylene bis-diphenyltriazine), and combinations thereof.

6. The sunscreen or daily care composition according to any one of items 1 to 5, wherein the composition is free of phenoxyethanol.

7. The sunscreen or daily care composition according to any one of items 1 to 6, wherein the composition comprises hexyl 2-[4-(diethylamino)-2-hydroxybenzoyl]benzoate (INCI diethylamino hydroxybenzoyl hexyl benzoate) in an amount of from 1% to 10% by weight, based on the total weight of the composition.

8. The sunscreen or daily care composition according to any one of items 1 to 7, wherein the composition comprises 1-(4-(1,1-dimethylethyl)phenyl)-3-(4-methoxyphenyl)propane-1,3-dione (INCI butyl methoxydibenzoylmethane) in an amount of from 1% to 5% by weight, based on the total weight of the composition.

9. The sunscreen or daily care composition according to any one of items 1 to 8, wherein the composition comprises the at least one organic particulate UV filter in an amount of from 0.5% to 10% by weight, based on the total weight of the composition.

10. The sunscreen or daily care composition according to any one of items 1 to 9, wherein the composition further comprises at least one UV filter selected from 4,4',4"-(1,3,5-triazine-2,4,6-triyltriimino)tris-benzoic acid-tris(2-ethylhexyl)ester (INCI ethylhexyl triazone), 4,4'-[[6-[[4-[[(1,1-dimethylethyl)amino]carbonyl]phenyl]amino]-1,3,5-triazin-2,4-diyl]diimino]bis-benzoic acid-bis(2-ethylhexyl)ester (INCI diethylhexyl-butamidotriazone), 2,4-bis-{[4-(2-ethyl-hexyloxy)-2-hydroxy]-phenyl}-6-(4-methoxyphenyl)-1,3,5 triazine (INCI bis-ethylhexyloxyphenol methoxyphenyl triazine) and combinations thereof.

11. The sunscreen or daily care composition according to any one of items 1 to 10, wherein the composition comprises perfume.

12. The sunscreen or daily care composition according to any one of items 1 to 11 comprising
  (i) hexyl 2-[4-(diethylamino)-2-hydroxybenzoyl]benzoate (INCI diethylamino hydroxybenzoyl hexyl benzoate); and
  (ii) 1-(4-(1,1-dimethylethyl)phenyl)-3-(4-methoxyphenyl)propane-1,3-dione (INCI butyl methoxydibenzoylmethane); and
  (iii) 2,2'-methylene bis[6-(2H-benzotriazol-2-yl)-4-(1,1,3,3-tetramethylbutyl)phenol] (INCI methylene bis-benzotriazolyl tetramethylbutylphenol);
wherein the composition does not comprise 2-hydroxy-4-methoxybenzophenone (INCI oxybenzone) and ethylhexyl-2-cyano-3,3-diphenyl-acrylate (INCI octocrylene).

13. The sunscreen or daily care composition according to item 12, wherein the composition comprises (iii) to (ii) in a ratio of 1:1.

14. The sunscreen or daily care composition according to item 12 or 13, wherein the composition comprises hexyl 2-[4-(diethylamino)-2-hydroxybenzoyl]benzoate (INCI diethylamino hydroxybenzoyl hexyl benzoate) in an amount of from 1% to 8% by weight, based on the total weight of the composition.

15. The sunscreen or daily care composition according to any one of items 12 to 14, wherein the composition comprises 1-(4-(1,1-dimethylethyl)phenyl)-3-(4-methoxyphenyl)propane-1,3-dione (INCI butyl methoxydibenzoylmethane) in an amount of from 1% to 5% by weight, based on the total weight of the composition.

16. The sunscreen or daily care composition according to any one of items 12 to 15, wherein the composition comprises 2,2'-methylene bis[6-(2H-benzotriazol-2-yl)-4-(1,1,3,3-tetramethylbutyl)phenol] (INCI methylene bis-benzotriazolyl tetramethylbutylphenol) in an amount of from 1% to 10% by weight, based on the total weight of the composition.

The invention claimed is:

1. A sunscreen or daily care composition comprising
  (i) hexyl 2-[4-(diethylamino)-2-hydroxybenzoyl]benzoate (INCI diethylamino hydroxybenzoyl hexyl benzoate) in an amount of from 2% to 8% by weight based on the total weight of the composition; and
  (ii) 1-(4-(1,1-dimethylethyl)phenyl)-3-(4-methoxyphenyl)propane-1,-3-dione (INCI butyl methoxydibenzoylmethane) in an amount of from 1% to 5% by weight, based on the total weight of the composition; and
  (iii) at least one organic particulate UV filter in an amount of from 0.5% to 10% by weight, based on the total weight of the composition; and
  (iv) at least one emollient with a polarity index of <30 mN/m,
  wherein the composition does not comprise 2-ethylhexyl-(2E)-3-(4-methoxyphenyl)acrylate (INCI ethylhexyl methoxy cinnamate), does not comprise isoamyl-4-methoxycinnamate (INCI isoamyl-p-methoxy cinnamate), does not comprise 2-hydroxy-4-methoxybenzophenone (INCI oxybenzone), does not comprise ethylhexyl-2-cyano-3,3-diphenyl-acrylate (INCI octocrylene) and does not comprise benzylidene malonates.

2. The sunscreen or daily care composition according to claim 1, wherein the composition is free of parabens.

3. The sunscreen or daily care composition according to claim 1, wherein the at least one organic particulate UV filter is selected from the group consisting of 2,2'-methylene bis[6-(2H-benzotriazol-2-yl)-4-(1,1,3,3-tetramethylbutyl)phenol] (INCI methylene bis-benzotriazolyl tetramethylbutylphenol), 2,4,6-tris(biphenyl-4-yl)-1,3,5-triazine (INCI trisbiphenyl triazine), 1,1'-(1,4-piperazinediyl)bis[1-[2-[4-(diethylamino)-2-hydroxybenzoyl]phenyl]-methanone (INCI bis-(diethylaminohydroxybenzoyl benzoyl)piperazine), 5,6,5',6'-tetraphenyl-3-3'-(1,4-phenylene)bis(1,2,4-triazine) (INCI phenylene bis-diphenyltriazine), micronized 1,4-di(benzoxazole-2'-yl)benzene and combinations thereof.

4. The sunscreen or daily care composition according to claim 3, wherein the at least one organic particulate UV filter is selected from the group consisting of 2,2'-methylene bis[6-(2H-benzotriazol-2-yl)-4-(1,1,3,3-tetramethylbutyl)phenol] (INCI methylene bis-benzotriazolyl tetramethylbutylphenol), 2,4,6-tris(biphenyl-4-yl)-1,3,5-triazine (INCI trisbiphenyl triazine), 5,6,5',6'-tetraphenyl-3-3'-(1,4-phenylene)bis(1,2,4-triazine) (INCI phenylene bis-diphenyltriazine), and combinations thereof.

5. The sunscreen or daily care composition according to claim 1, wherein the composition is free of phenoxyethanol.

6. The sunscreen or daily care composition according to claim 1, wherein the composition further comprises at least one UV filter selected from 4,4',4"-(1,3,5-triazine-2,4,6-triyltriimino)tris-benzoic acid-tris(2-ethylhexyl)ester (INCI ethylhexyl triazone), 4,4'-[[6-[[4-[[(1,1-dimethylethyl)amino]carbonyl]phenyl]amino]-1,3,5-triazin-2,4-diyl]diimino]bis-benzoic acid-bis(2-ethylhexyl)ester (INCI diethylhexyl-butamidotriazone), 2,4-bis-{[4-(2-ethyl-hexyloxy)-2-hydroxy]-phenyl}-6-(4-methoxyphenyl)-1,3,5 triazine (INCI bis-ethylhexyloxyphenol methoxyphenyl triazine) and combinations thereof.

7. The sunscreen or daily care composition according to claim 1, wherein the composition comprises at least one perfume.

8. The sunscreen or daily care composition according to claim 1, wherein the at least one particulate UV filter (iii) is 2,2'-methylene bis[6-(2H-benzotriazol-2-yl)-4-(1,1,3,3-tetramethylbutyl)phenol] (INCI methylene bis-benzotriazolyl tetramethylbutylphenol).

9. The sunscreen or daily care composition according to claim 1, wherein the composition comprises (iii) to (ii) in a ratio of 1:1.

10. The sunscreen or daily care composition according to claim 1, wherein the at least one emollient with a polarity index of <30 mN/m is selected from esters of linear or branched fatty acids with linear or branched fatty alcohols, di- and tricarboxylic acid esters with linear or branched alcohols, esters of hydroxycarboxylic acids with linear or branched fatty alcohols, esters of linear or branched fatty acids with polyhydric alcohol and mono-, di-, and triglycerides based on $D_6$-$D_{18}$ fatty acids.

11. A method comprising incorporating hexyl 2-[4-(diethylamino)-2-hydroxybenzoyl]benzoate (INCI diethylamino hydroxybenzoyl hexyl benzoate) and at least one organic particulate UV filter for photostabilizing 1-(4-(1,1-dimethylethyl)phenyl)-3-(4-methoxyphenyl)propane-1,3-dione (INCI butyl methoxydibenzoylmethane) into a sunscreen or daily care composition, wherein the composition does not comprise 2-ethylhexyl-(2E)-3-(4-methoxyphenyl)acrylate (INCI ethylhexyl methoxy cinnamate), does not comprise isoamyl-4-methoxycinnamate (INCI isoamyl-p-methoxy cinnamate), does not comprise 2-hydroxy-4-methoxybenzophenone (INCI oxybenzone) and does not comprise ethylhexyl-2-cyano-3,3-diphenyl-acrylate (INCI octocrylene).

12. The sunscreen or daily care composition according to claim 1, wherein the composition comprises hexyl 2-[4-(diethylamino)-2-hydroxybenzoyl]benzoate (INCI diethylamino hydroxybenzoyl hexyl benzoate) in an amount of from 4% to 6% by weight based on the total weight of the composition.

13. A sunscreen or daily care composition comprising
   (i) hexyl 2-[4-(diethylamino)-2-hydroxybenzoyl]benzoate (INCI diethylamino hydroxybenzoyl hexyl benzoate) in an amount of from 1% to 9% by weight based on the total weight of the composition; and
   (ii) 1-(4-(1,1-dimethylethyl)phenyl)-3-(4-methoxyphenyl)propane-1,-3-dione (INCI butyl methoxydibenzoylmethane); and
   (iii) at least one organic particulate UV filter; and
   (iv) at least one emollient with a polarity index of <30 mN/m selected from the group consisting of esters of linear or branched fatty acids with linear or branched fatty alcohols; esters of aromatic carboxylic acids with linear or branched fatty alcohols; di- and tricarboxylic acid esters with linear or branched alcohols; esters of hydroxycarboxylic acids with linear or branched fatty alcohols; esters of linear or branched fatty acids with polyhydric alcohol,
   wherein the composition does not comprise 2-ethylhexyl-(2E)-3-(4-methoxyphenyl)acrylate (INCI ethylhexyl methoxy cinnamate), does not comprise isoamyl-4-methoxycinnamate (INCI isoamyl-p-methoxy cinnamate), does not comprise 2-hydroxy-4-methoxybenzophenone (INCI oxybenzone), does not comprise ethylhexyl-2-cyano-3,3-diphenyl-acrylate (INCI octocrylene) and does not comprise benzylidene malonates.

* * * * *